United States Patent
Tan et al.

(10) Patent No.: US 10,758,444 B2
(45) Date of Patent: Sep. 1, 2020

(54) SYSTEM AND METHOD OF APPLYING A MASSAGE AND EMITTING AN AROMATIC SCENT

(71) Applicant: OSIM International Ltd, Singapore (SG)

(72) Inventors: Kia Tong Tan, Singapore (SG); Gilbert Casurog Realuyo, Singapore (SG); Evan Chee, Singapore (SG)

(73) Assignee: OSIM INTERNATIONAL LTD, Singapore (SG)

( * ) Notice: Subject to any disclaimer, the term of this patent is extended or adjusted under 35 U.S.C. 154(b) by 620 days.

(21) Appl. No.: 15/101,318

(22) PCT Filed: Mar. 12, 2015

(86) PCT No.: PCT/SG2015/000072
§ 371 (c)(1),
(2) Date: Jun. 2, 2016

(87) PCT Pub. No.: WO2016/144253
PCT Pub. Date: Sep. 15, 2016

(65) Prior Publication Data
US 2017/0007488 A1    Jan. 12, 2017

(51) Int. Cl.
*A61H 1/00* (2006.01)
*A61L 9/03* (2006.01)
(Continued)

(52) U.S. Cl.
CPC .......... *A61H 1/008* (2013.01); *A61H 9/0078* (2013.01); *A61L 9/03* (2013.01); *A61L 9/032* (2013.01);
(Continued)

(58) Field of Classification Search
CPC .............. A61H 1/008; A61H 7/00–008; A61H 9/00–0007; A61H 9/0078; A61H 9/0092;
(Continued)

(56) References Cited

U.S. PATENT DOCUMENTS 4,841,954 A    6/1989    Kalsi
5,810,253 A    9/1998    Ohayon
(Continued)

FOREIGN PATENT DOCUMENTS

CA    2668217 A1    12/2010
CN    201304074 Y    9/2009
(Continued)

OTHER PUBLICATIONS

Official Action from Taiwanese Patent Application No. 105107075 dated Feb. 7, 2017.
(Continued)

*Primary Examiner* — Rachel T Sippel
(74) *Attorney, Agent, or Firm* — Baker & McKenzie LLP

(57) ABSTRACT

A massage apparatus includes a massage system, a scent-emitting module, and a microcontroller respectively connected with the massage system and the scent delivery module, the microcontroller being operable to activate the massage system to apply a massage action and to activate the scent-emitting module to emit an aromatic scent.

15 Claims, 11 Drawing Sheets

(51) Int. Cl.
*A61H 9/00* (2006.01)
*A61H 23/00* (2006.01)
*A61H 7/00* (2006.01)
*A61M 21/02* (2006.01)
*A61M 21/00* (2006.01)
*A61M 11/04* (2006.01)

(52) U.S. Cl.
CPC ............. *A61M 21/02* (2013.01); *A61H 7/007* (2013.01); *A61H 23/006* (2013.01); *A61H 2201/0207* (2013.01); *A61H 2201/102* (2013.01); *A61H 2201/1215* (2013.01); *A61H 2201/5035* (2013.01); *A61H 2205/024* (2013.01); *A61L 2209/111* (2013.01); *A61L 2209/133* (2013.01); *A61M 11/042* (2014.02); *A61M 2021/0016* (2013.01); *A61M 2021/0022* (2013.01)

(58) Field of Classification Search
CPC ........ A61H 23/00–04; A61H 39/00–04; A61H 2201/0103; A61H 2201/0149; A61H 2201/0207; A61H 2201/102; A61H 2201/1215; A61H 2201/1604–1607; A61H 2201/165–1652; A61H 2201/5035; A61H 2205/024; A61L 9/00; A61L 9/015–04; A61L 9/12–127; A61L 2209/111; A61L 2209/133–134; A61M 21/02; A61M 11/04–047; A61M 2021/0016; A61M 2021/0022; A45D 34/02; B05B 7/1686
See application file for complete search history.

(56) References Cited

U.S. PATENT DOCUMENTS

| | | | |
|---|---|---|---|
| 10,022,511 B2* | 7/2018 | Avni | A61H 15/0085 |
| 2002/0048530 A1* | 4/2002 | Wohrle | A61L 9/035 422/22 |
| 2003/0162595 A1* | 8/2003 | Serbanescu | A61H 19/34 472/1 |
| 2006/0175426 A1* | 8/2006 | Schramm | A01M 1/2033 239/69 |
| 2006/0258963 A1 | 11/2006 | Kopanic, Jr. et al. | |
| 2008/0183113 A1 | 7/2008 | Kazerounian et al. | |
| 2009/0216070 A1* | 8/2009 | Hunt | H04N 5/775 600/27 |
| 2011/0004048 A1 | 1/2011 | Brunelle | |
| 2011/0055720 A1 | 3/2011 | Potter et al. | |
| 2016/0295919 A1* | 10/2016 | Thomas, Jr. | A24F 47/008 |
| 2017/0042439 A1* | 2/2017 | Yeow | G16H 10/60 |
| 2017/0135492 A1* | 5/2017 | Biancofiore | A47C 21/003 |

FOREIGN PATENT DOCUMENTS

| | | |
|---|---|---|
| JP | 1991-033620 U | 4/1991 |
| JP | 2000-350757 A | 12/2000 |
| JP | 2003169830 A | 6/2003 |
| JP | 2003-180839 A | 7/2003 |
| JP | 2008-279015 A | 11/2008 |
| JP | 2009-517170 A | 4/2009 |
| KR | 1020090099686 A | 9/2009 |
| TW | M251600 U | 12/2004 |
| TW | M263937 U | 5/2005 |

OTHER PUBLICATIONS

An Examination report issued by the Australian Patent Office dated Jan. 30, 2017 in connection with Australian Patent Application No. 2015341419.
Written Opinion of the International Searching Authority, PCT/SG2015/000072, dated Jun. 5, 2015, 6 pages.
International Search Report, PCT/SG2015/000072, dated Jun. 5, 2015, 4 pages.
International Preliminary Report on Patentability, dated Feb. 10, 2016, 14 pages.
Office Action from Japanese Patent Office in Japanese Application No. 2016-544501, dated Jan. 8, 2019. (Original Japanese and English translation).

* cited by examiner

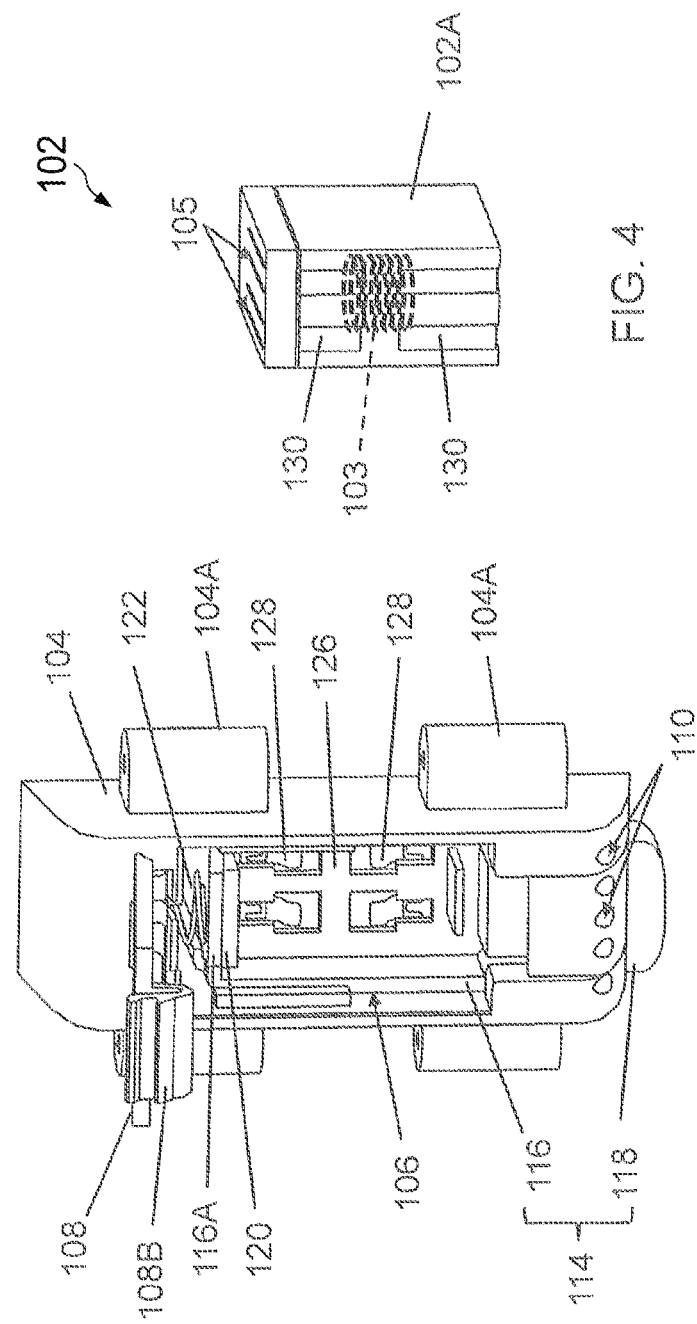

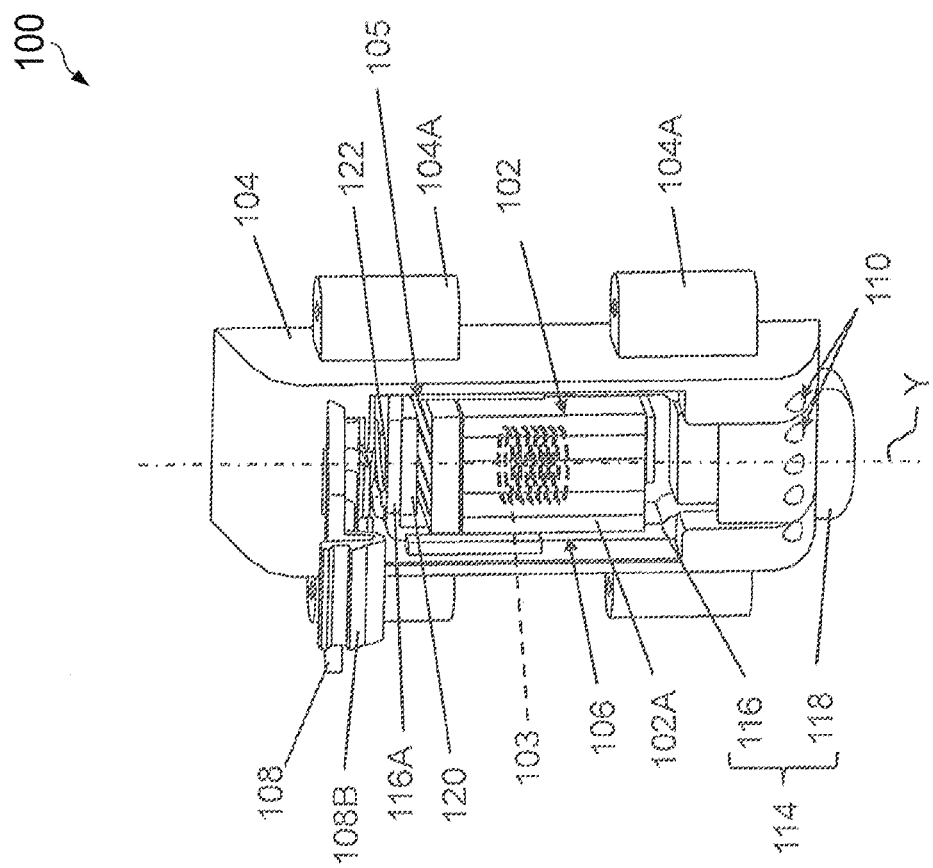

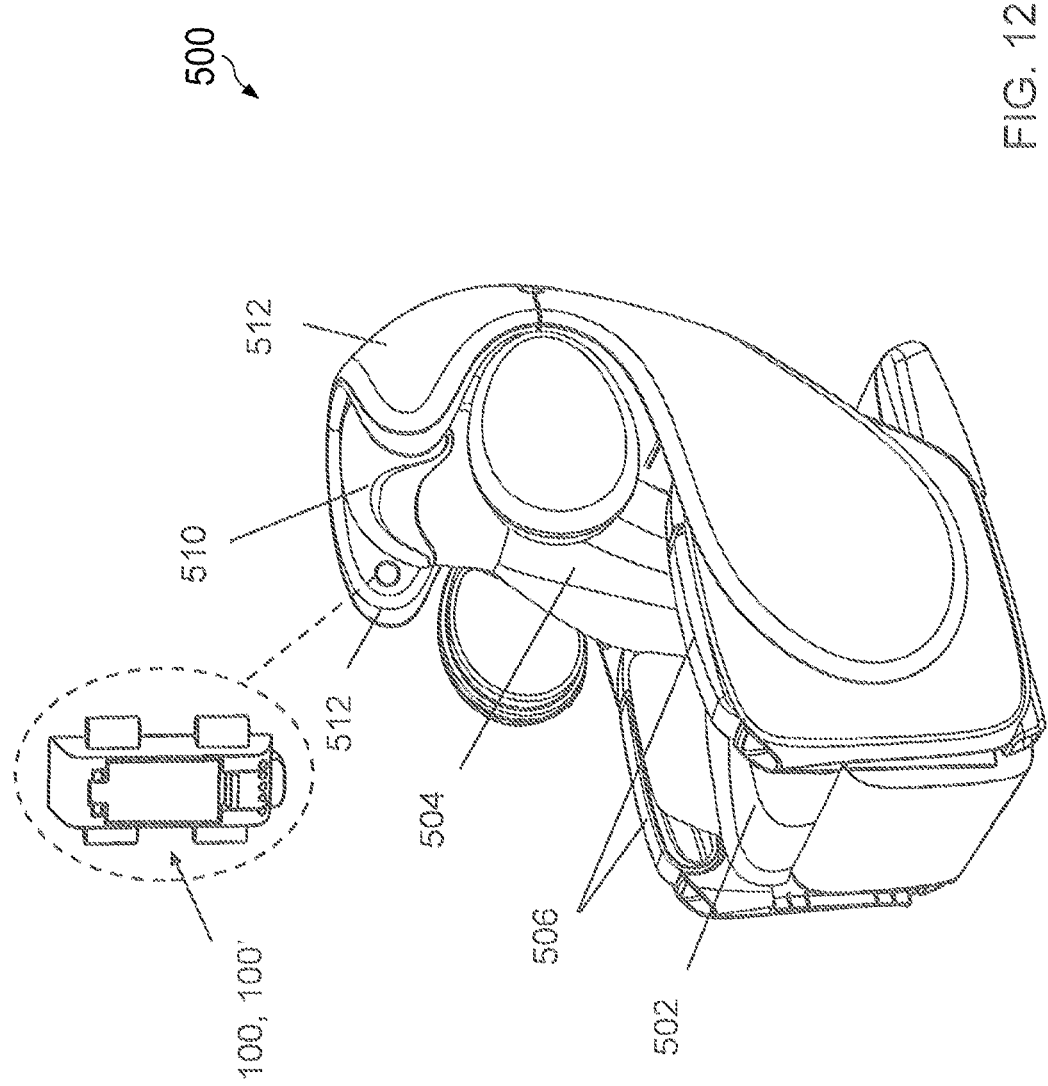

SYSTEM AND METHOD OF APPLYING A MASSAGE AND EMITTING AN AROMATIC SCENT

CROSS-REFERENCE TO RELATED APPLICATION(S)

This patent application is a national phase filing under section 371 of PCT/SG2015/000072, filed Mar. 12, 2015, which is incorporated herein by reference in its entirety.

BACKGROUND

1. Field of the Invention

The present invention generally relates to massage apparatuses having scent-emitting modules.

2. Description of the Related Art

Massage apparatuses currently available on the market are equipped with a massage member capable of applying diverse types of massage actions on a user's body. According to the needs, a user may select a massage program corresponding to a predetermined combination of movement and pressure actions of the massage member for producing certain desirable relaxing effects. However, the mere application of massage actions may not provide sufficient relaxing results.

Therefore, there is a need for massage apparatuses that can address at least the foregoing issues.

SUMMARY

The present application describes a massage apparatus that can enhance massage actions using aromatherapy to provide enhanced relaxation effects. In one embodiment, the massage apparatus includes a massage system, a scent-emitting module, and a microcontroller respectively connected with the massage system and the scent delivery module, the microcontroller being operable to activate the massage system to apply a massage action and to activate the scent-emitting module to emit an aromatic scent.

In another embodiment, the massage apparatus includes a massage system, a scent-emitting module, and a microcontroller operable to execute a massage program on the massage system for applying a sequence of massage actions on a user's body, the massage program including an instruction to activate the scent-emitting module for emitting an aromatic scent.

In yet another embodiment, a method of applying a massage through a massage apparatus is described. The method includes performing a first sequence of massage actions, while performing the first sequence of massage actions causing the massage apparatus to emit a first aromatic scent, performing a second sequence of massage actions, and while performing the second sequence of massage actions causing the massage apparatus to emit a second aromatic scent.

Advantages of the systems and methods described herein include the ability to apply massage actions and emit an aromatic scent so as to effectively relieve stress and provide enhanced relaxation effects. As a result, a user can enjoy enhanced massage experience and obtain effective relaxation.

BRIEF DESCRIPTION OF THE DRAWINGS

FIG. 3 is a schematic view illustrating the scent-emitting module with no scent cartridge installed therein;

FIG. 4 is a schematic view illustrating a scent cartridge alone;

FIG. 5 is a schematic view illustrating the scent cartridge in an opened state for emitting an aromatic scent;

FIG. 12 is a schematic view illustrating s massage chair including the scent-emitting module.

DETAILED DESCRIPTION OF THE EMBODIMENTS

Figure 1:
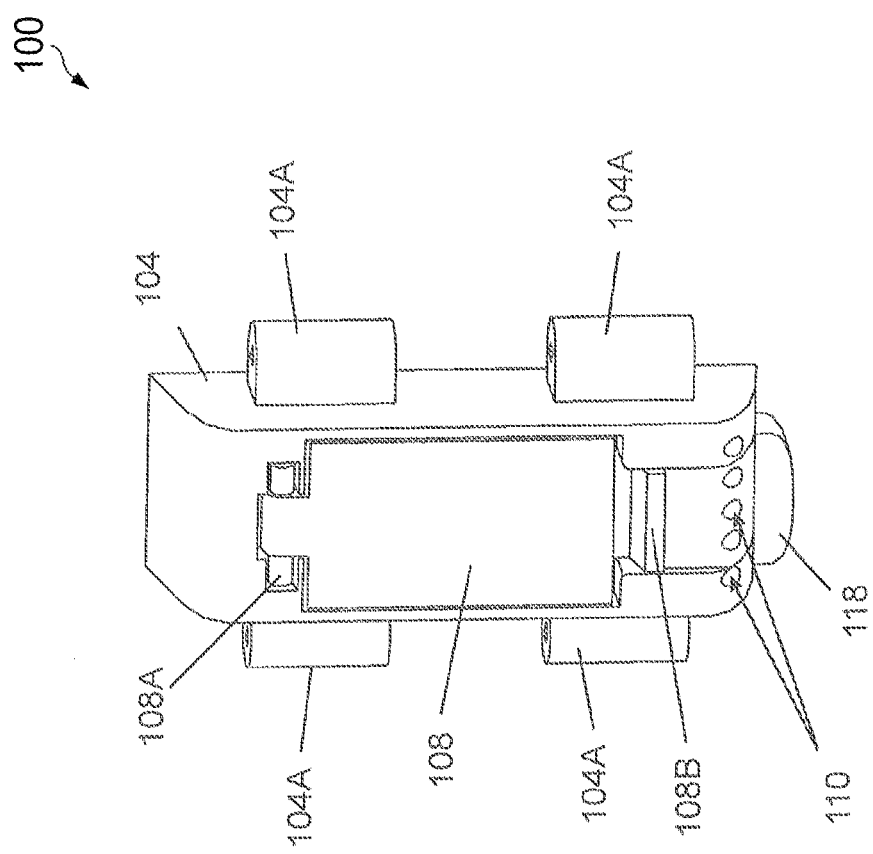
FIG. 1 is a schematic view illustrating an embodiment of a scent-emitting module suitable for use in a massage apparatus.

The present application describes massage apparatuses that integrate scent-emitting modules operable to diffuse an aromatic scent while a massage action is applied on a user. The combined application of massage actions and aromatherapy can produce enhanced relaxing effects.

FIGS. 1-5 schematic views illustrating a scent-emitting module 100 for use in a massage apparatus. The seen emitting module 100 can include a scent cartridge 102 and a housing 104. The scent cartridge 102 can be a casing 102A containing a scent medium for diffusing a desirable scent. Examples of the scent medium can include-aromatic oil, gel or compressed aromatic in liquid form, and the aromatic scent can be lemon scent, mint scent, etc. In one embodiment, the scent cartridge 102 may include a heater 103 (shown with phantom lines in FIG. 2) operable to heat the scent medium for producing aromatic vapor, the heater 103 being an exemplary heating resistor. In another embodiment, the scent medium may be diffused through a porous member (not shown) arranged inside the scent cartridge 102. The aromatic scent produced by the sent medium can be emitted out of the scent cartridge 102 through one or more outlet holes 105 provided at a side of the scent cartridge 102.

The housing 104 can exemplary have a generally elongated shape, but any shapes can be applicable general. The housing 104 can have one or more mount structure 104A for facilitating the assembly and attachment of the scent-emitting module 100 in a massage apparatus. Moreover, the housing 104 can have a cavity 106 in which the scent cartridge 102 can be removably arranged, and can be assembled with a lid 108. The lid 108 is operable to open the housing 104 and allow access to the cavity 106 for installation or removal of the scent cartridge 102, and close the housing 104 to prevent access to the cavity 106 once the scent cartridge 102 is installed therein. In one embodiment, the lid 108 can have a first end portion 108A pivotally connected with the housing 104, and a second end portion forming a resilient tab 108B that can engage with a rim of the cavity 106 to hold the lid 108 in a closed position.

The housing 104 can have one or more outlet holes 110 connecting to the cavity 106 through which scent exiting the scent cartridge 102 can be emitted out of the scent-emitting module 100 by diffusion. The outlet holes 110 may be arranged at any desirable position on the housing 104 for facilitating diffusion of the scent to a proximate environment outside the scent-emitting module 100. For example, the outlet holes 110 may be arranged at a side of the cavity 106 opposite to that of the first end portion 108A of the lid 108. Outlet holes 110 may be arranged at about a bottom portion of the housing which is at about the second end portion 108A of the lid 108 when in the closed position.

Figure 2:
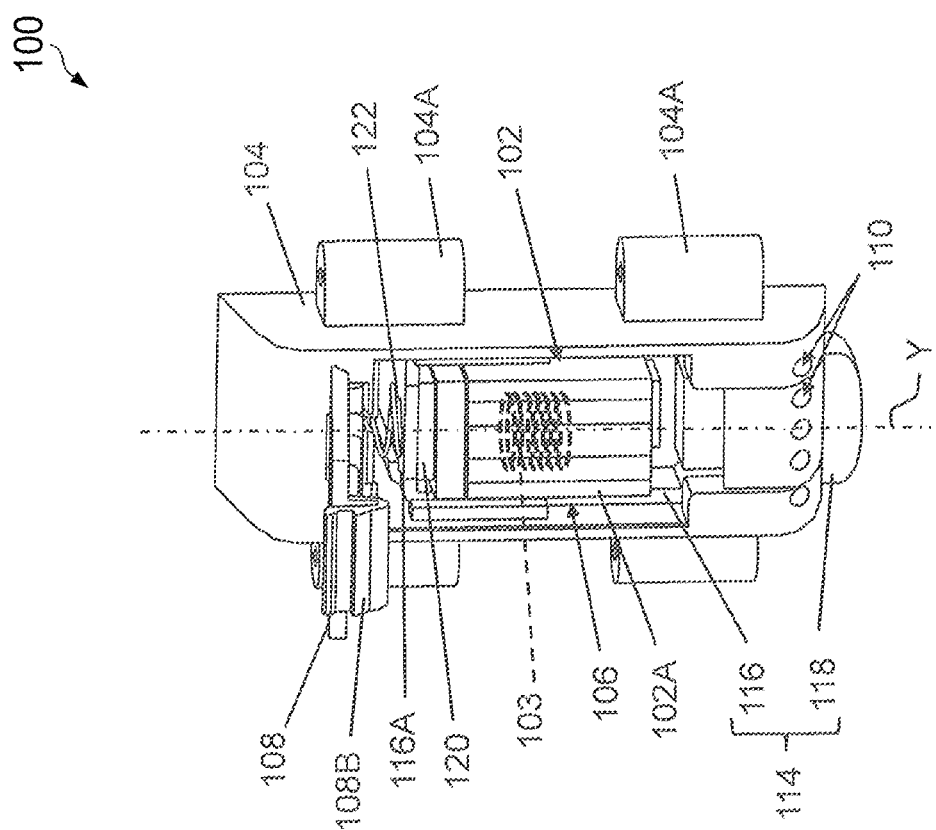
FIG. 2 is a schematic view illustrating the scent-emitting module installed with a scent cartridge

Referring to FIGS. 1-5, the housing 104 can be further connected with a scent release actuator 114 operable to open or close the outlet holes 110 to allow or disable scent emission out of the housing 104. The scent release actuator 114 can include a frame 116 and an operating portion 118 connected with each other. In one embodiment, the scent release actuator 114 comprised of the frame 116 and the operating portion 118 may be formed integrally as a single body (as shown in FIG. 2). In other embodiments not shown, the frame 116 and the operating portion 118 may be two distinct components operatively connected with each other. The scent release actuator 114 can be assembled with the housing 104 for sliding movement, the frame 116 being arranged inside the cavity 106, the operating portion 118 being exposed outward for manual operation. In one example of construction, the housing 104 may have a longitudinal axis Y, the scent release actuator 114 can slide relative to the housing 104 along the longitudinal axis Y, and the lid 108 can pivot relative to the housing 104 about a pivot axis extending transversally with respect to the longitudinal axis Y. Longitudinal axis Y may extend from a top portion to a bottom portion of the scent emitting module 100.

The frame 116 can surround the scent cartridge 102 placed inside the cavity 106, and can have a distal segment 116A affixed with a sealing member 120. The sealing member 120 may be exemplary made of rubber, or other adequate materials, e.g resilient material. The scent release actuator 114 can slide relative to the housing 104 between two positions: a first position where the sealing member 120 closes the holes 105 of the scent cartridge 102 to block scent emission (as better shown in FIG. 2), and a second position where the sealing member 120 is displaced away from the holes 105 to allow scent emission (as better shown in FIG. 5). When the scent release actuator 114 is in the opened position, the spring 122 is compressed, and the scent can exit the scent cartridge 102 through the outlet holes 105, diffuse inside the housing 104, and exit the scent-emitting module 100 via the outlet holes 110.

Scent release actuator 114 may be biased by a biasing member within the housing 104. For example, a spring 122 can be provided to bias the scent release actuator 114 to the first position sealing the holes 105 of the scent cartridge 102. The spring 122 can be respectively connected with the housing 104 and the scent release actuator 114, e.g., the distal segment 116A of the frame 116. Moreover, the scent release actuator 114 may be provided with a detent (not shown) that can engage with the housing 104 to hold the scent release actuator 114 in the second position opening the outlet holes 105 of the scent cartridge 102.

The operating portion 118 may be exposed outside the housing 104 for facilitating manual operation of the scent release actuator 114. In one embodiment, the operating portion 118 may be exemplary disposed near the outlet holes 110 of the housing 104.

While the scent release actuator 114 has been described as being manually operated to open and seal the scent cartridge 102, alternate embodiments may have the scent release actuator 114 electrically or pneumatically controlled to open and seal the scent cartridge 102. For example, in certain embodiment, the scent cartridge 102 may use compressed aromatic gas as scent medium and a valve that holds the pressured aromatic gas in the scent cartridge 102, and the scent release actuator 114 can be electrically controlled to press and open the valve to release the aromatic scent in mist form.

Referring to FIGS. 3 and 4, in an embodiment where the scent cartridge 102 is activated by heating, the housing 104 can further have an inner sidewall 126 provided with a plurality of electric conductors 128, and the scent cartridge 102 can have a plurality of electric terminals 130 (i.e., anode and cathode) that are connected with the heater 103 embedded in the scent cartridge 102. When the scent cartridge 102 is installed in the cavity 106 of the housing 104, the electric terminals 130 of the scent cartridge 102 can be in electric contact with the electric conductors 128 of the housing 104 so that an electric current can be flowed through the heater 103 to heat the scent medium and produce aromatic vapor.

While the scent-emitting module 100 has been exemplarily described to receive one scent cartridge 102, it will be understood that the size of the housing 104 may be modified to receive multiple scent cartridges 102. In this case, the scent release actuator 114 can be likewise configured to close or open all the scent cartridges 102 in a concurrent manner.

Figure 6:
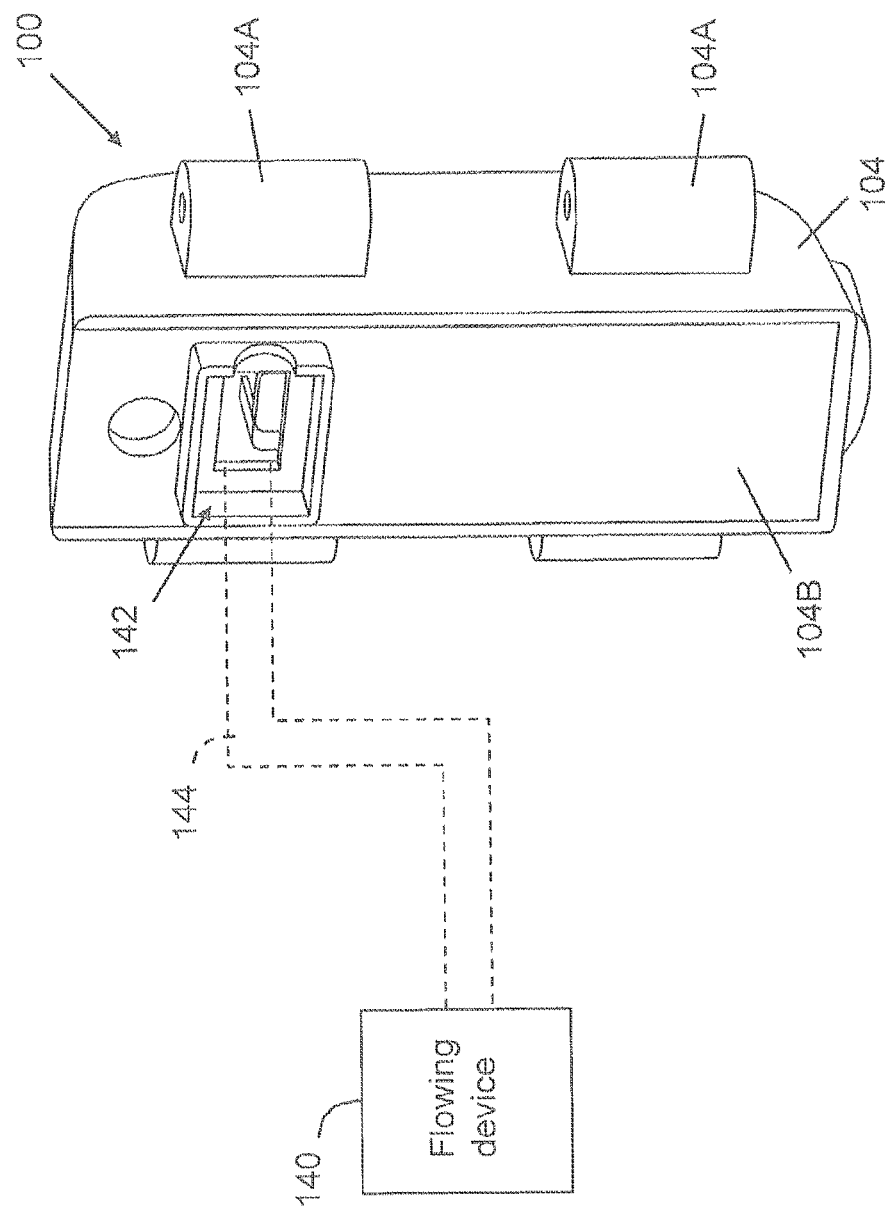
FIG. 6 is a simplified schematic view illustrating a connection between the housing of the scent-emitting module and a flowing device.
Figure 7:
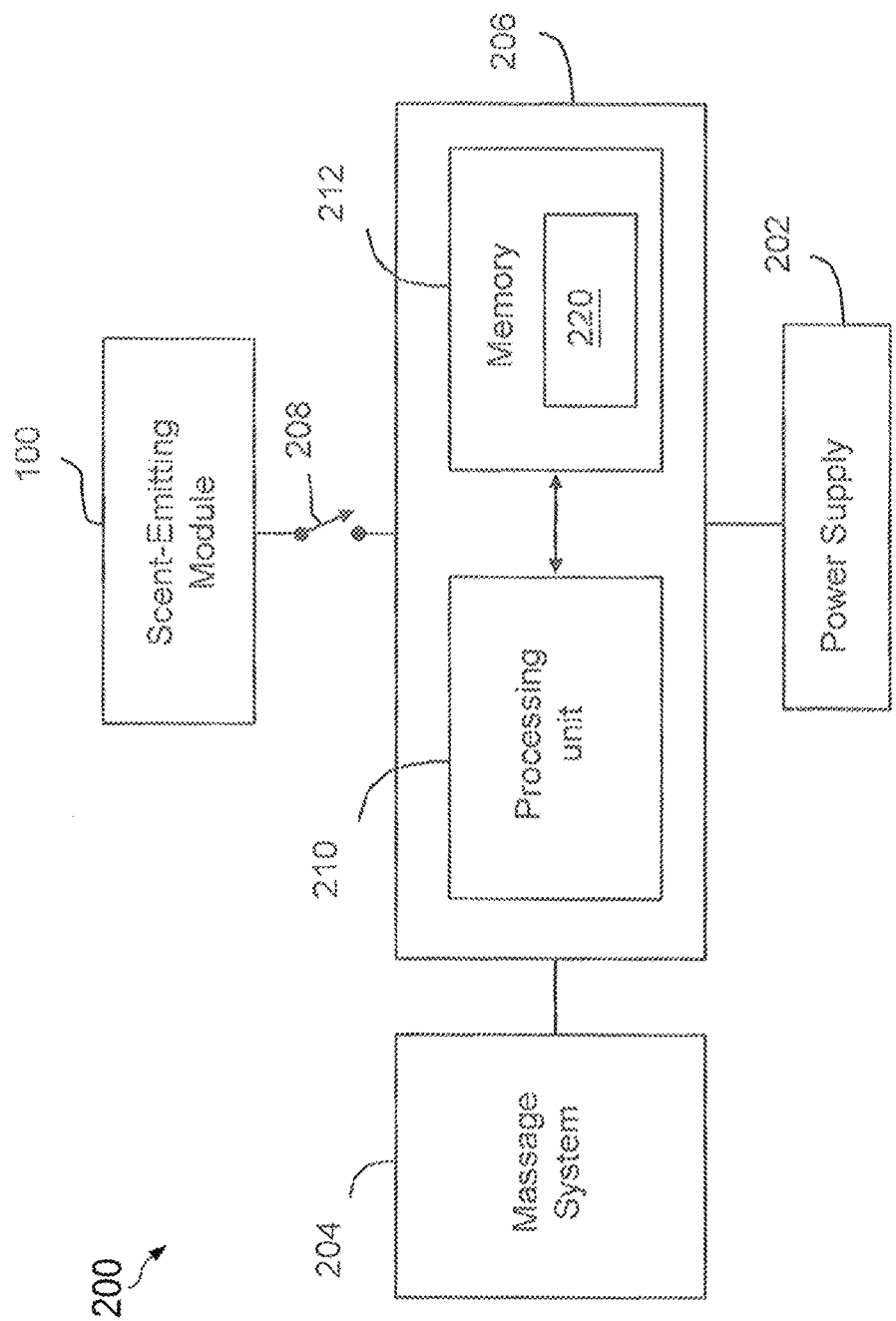
FIG. 7 is a simplified block diagram illustrating one embodiment of a massage apparatus operable to emit an aromatic scent.
Figure 8:
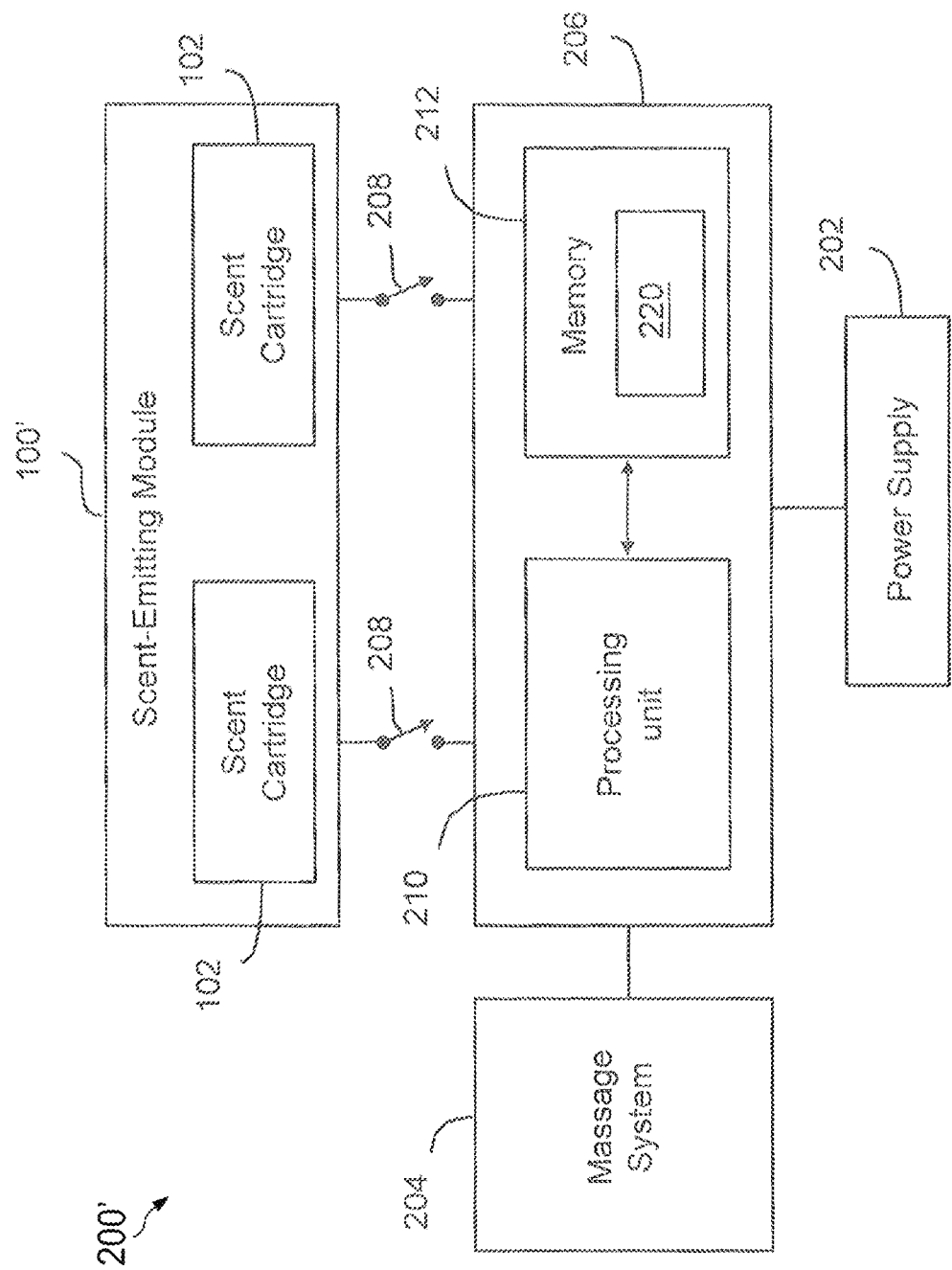
FIG. 8 is a simplified block diagram illustrating a variant embodiment of a massage apparatus operable to selectively emit one or more aromatic scents.
Figure 10:
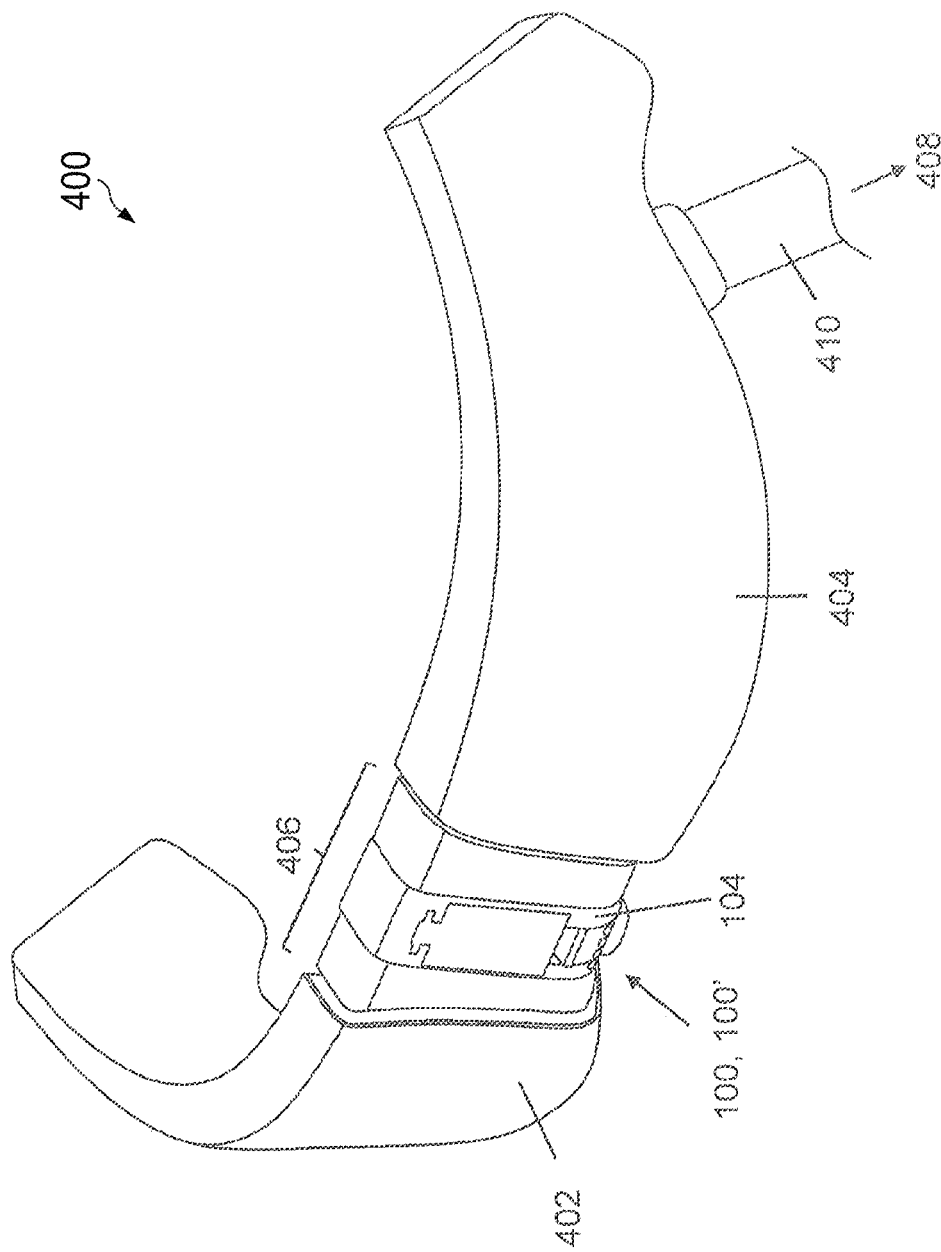
FIG. 10 is a schematic view illustrating an eye massage apparatus including the scent-emitting module.

The aromatic scent can be typically conveyed by diffusion to a proximate outer environment near the scent-emitting module 100. In some embodiments, a flowing device may be provided for facilitating outward diffusion of the aromatic scent from the housing 104, such as an electric fan, air pump or blower device. For example, the flowing device may be arranged outside the housing 104, and air flow may be transported along a duct from the flowing device to the interior of the housing 104. FIG. 6 is a simplified schematic view illustrating a connection between the housing 104 of the scent-emitting module 100 and a flowing device 140. A rear surface 104B of the housing 104 opposite to the side of the lid 108 may exemplary have an opening 142, and a duct 144 can be connected with the opening 142 of the housing 104 and the flowing device 140 disposed remotely from the housing 104. As the scent-emitting module 100 produces a scent, the flowing device 140 can create an air flow through the duct 144 into the housing 104 to promote outward diffusion of the scent through the outlet holes 110 thereof. Exemplary implementation of a massage apparatus having a flowing device is described hereinafter with reference to FIGS. 10 and 11.

In conjunction with FIGS. 1-6, FIG. 7 is a simplified block diagram illustrating one embodiment of a massage apparatus 200 incorporating the scent-emitting module 100 described previously. The massage apparatus 200 can include a power supply 202, a massage system 204, a microcontroller 206 and the scent-emitting module 100 previously described. The massage system 204 can include components such as actuating arms, electric motors, airbag pumps, solenoids, etc. operable to apply various types of massage actions. Examples of massage actions that may be applied by the sage system 204 can include, without limitation, tapping actions, kneading massage actions, gripping actions and rolling actions.

The microcontroller 206 can be connected with the massage system 204, and can control and supervise the operation of the massage system 204 to apply various massage actions. Moreover, the microcontroller 206 can be connected with the scent-emitting module 100 via a switch 208, which can be operated to activate or deactivate the scent-emitting module 100 for selective scent emission. In one embodiment, the microcontroller 206 can exemplarily be a 32-bit Reduced Instruction Set Computing (RISC) microcontroller. The microcontroller 206 can select one of a plurality of massage programs stored internally, and execute the selected massage program on the massage system 204. In one embodiment, the microcontroller 206 can exemplarily include a processing unit 210, and a Memory 212 for storing massage program codes.

The memory 212 can store the codes of multiple massage programs 220 available in the massage apparatus 200. Each of the massage programs 220 can be executable by the processing unit 210 so as to actuate the massage system 204 to perform a sequence of predetermined massage actions on a user's body. One or more of the massage programs 220 may further include an instruction executable by the processing unit 210 to activate the scent-emitting module 100, such that an aromatic scent may be emitted while the massage system 204 applies a massage action on the user's body. Accordingly, the user can inhale the aromatic scent while receiving the massage actions, which can provide enhanced relaxing results.

In conjunction with FIGS. 1-7, FIG. 8 is a schematic view, illustrating a variant embodiment of a massage apparatus 200' operable to emit multiple aromatic scents. In this embodiment, the scent-emitting module 100' can be sized to receive multiple scent cartridges 102 of different scents. The scent-emitting module 100' can be similar to the scent-emitting module 100 described in FIGS. 1-6, except that the housing 104 can be sized to receive multiple scent cartridges 102. The multiple scent cartridges 102 may be respectively connected with distinctive and separate sets of the electric conductors 128 (better shown in FIG. 3), which are respectively connected with the microcontroller 206 via a plurality of switches 208. In the massage apparatus 200', the microcontroller 206 can operate one or more of the switches 208 to activate the scent-emitting module 100 for selectively emitting one or more scents.

Figure 9:
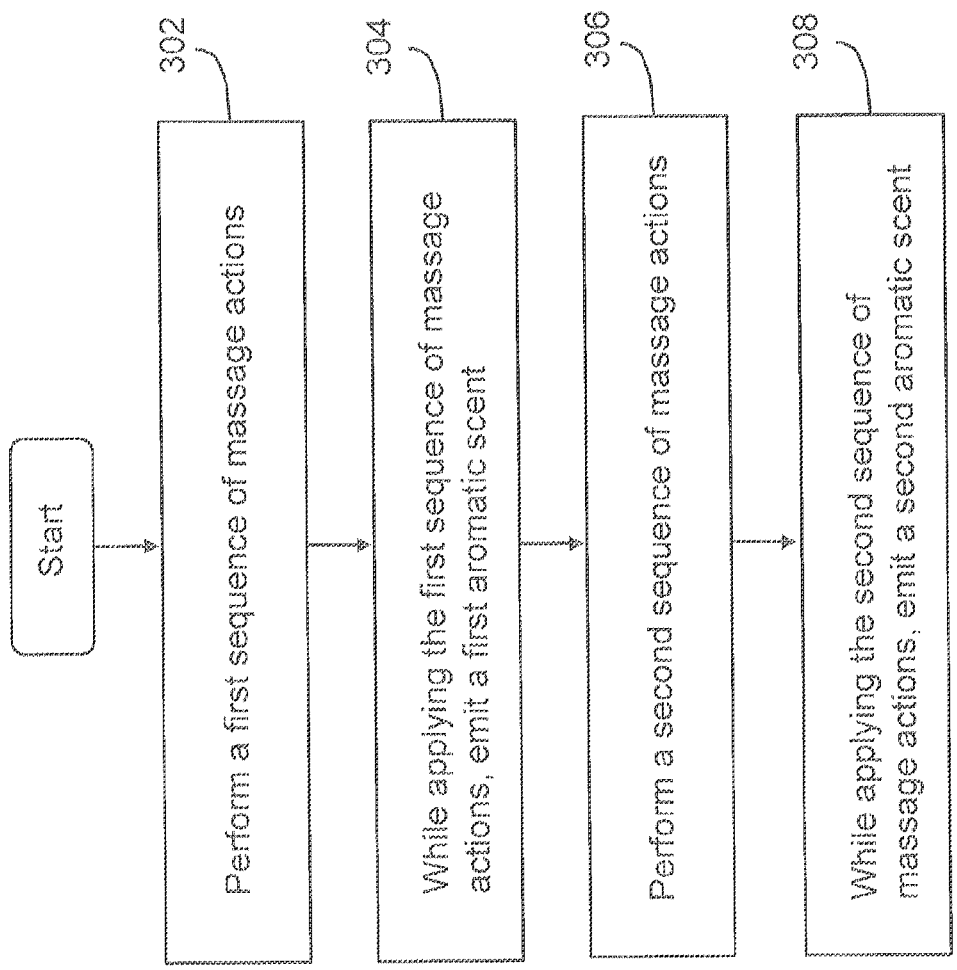
FIG. 9 is a flowchart illustrating exemplary method steps implemented in a massage apparatus incorporating a scent-emitting module.

FIG. 9 is a flowchart illustrating exemplary steps of a massage program implemented on the massage apparatus 200'. In initial step 302, the microcontroller 206 can actuate the massage system 204 to perform a first sequence of massage actions on a selected region of a user's body. In step 304, while the first sequence of massage actions are applied on the user, the microcontroller 206 can further activate the scent-emitting module 100' to produce a first scent. The first scent can exemplarliy be lemon scent. Moreover, the scent-emitting module 100' in step 304 may be activated continuously, or repeatedly switched on and off to controllably adjust the amount of scent emitted during the application of the first sequence of massage actions. In step 306, the microcontroller 206 cart actuate the massage system 204 to perform a second sequence of massage actions. In step 308, while the second sequence of massage actions are applied, the microcontroller 206 can activate the scent-emitting module 100' to produce a second scent different from the first scent. The second scent can exemplary be mint scent. Likewise, the scent-emitting module 100' in step 308 may be activated continuously, or repeatedly switched on and off to controllably adjust the amount of scent emitted during the application of the second sequence of massage actions. Accordingly, the massage apparatus 200' can apply massage actions, and selectively emit an aromatic scent associated with the massage actions in a synchronous manner. First scent and second scent may be configured to be activated at the same time to have a combined scent. First scent and second scent may be diffused in varying ratio, e.g. 50%-50%, 40%-60%, 30%-70%, 20%-80% to provide a variety of combination of scents.

Different types of massage apparatuses incorporating the scent-emitting modules as described previously may be implemented. In conjunction with FIGS. 1-7, FIGS. 10 and 11 are schematic views illustrating an eye massage apparatus 400 including the scent-emitting module 100 or 100'. The eye massage apparatus 400 can include a left-eye portion 402, a right-eye portion 404, and a bridge region 406 that connects the left-eye portion 402 with the right-eye portion 404. Each of the left-eye portion 402 and the right-eye portion 404 can include a massage mechanism operable to apply a massage action to a region around the user's eye. The scent-emitting module 100 or 100' can be arranged in the bridge region 406 above the nasal bridge of a user. In particular, the scent-emitting module 100 or 100' can be placed with the outlet holes 110 of the housing 104 turned downward toward the user's nose. The proximity of the outlet holes 110 to the user's nose can allow efficient delivery of the scent, and reduce waste induced by dispersion.

Figure 11:
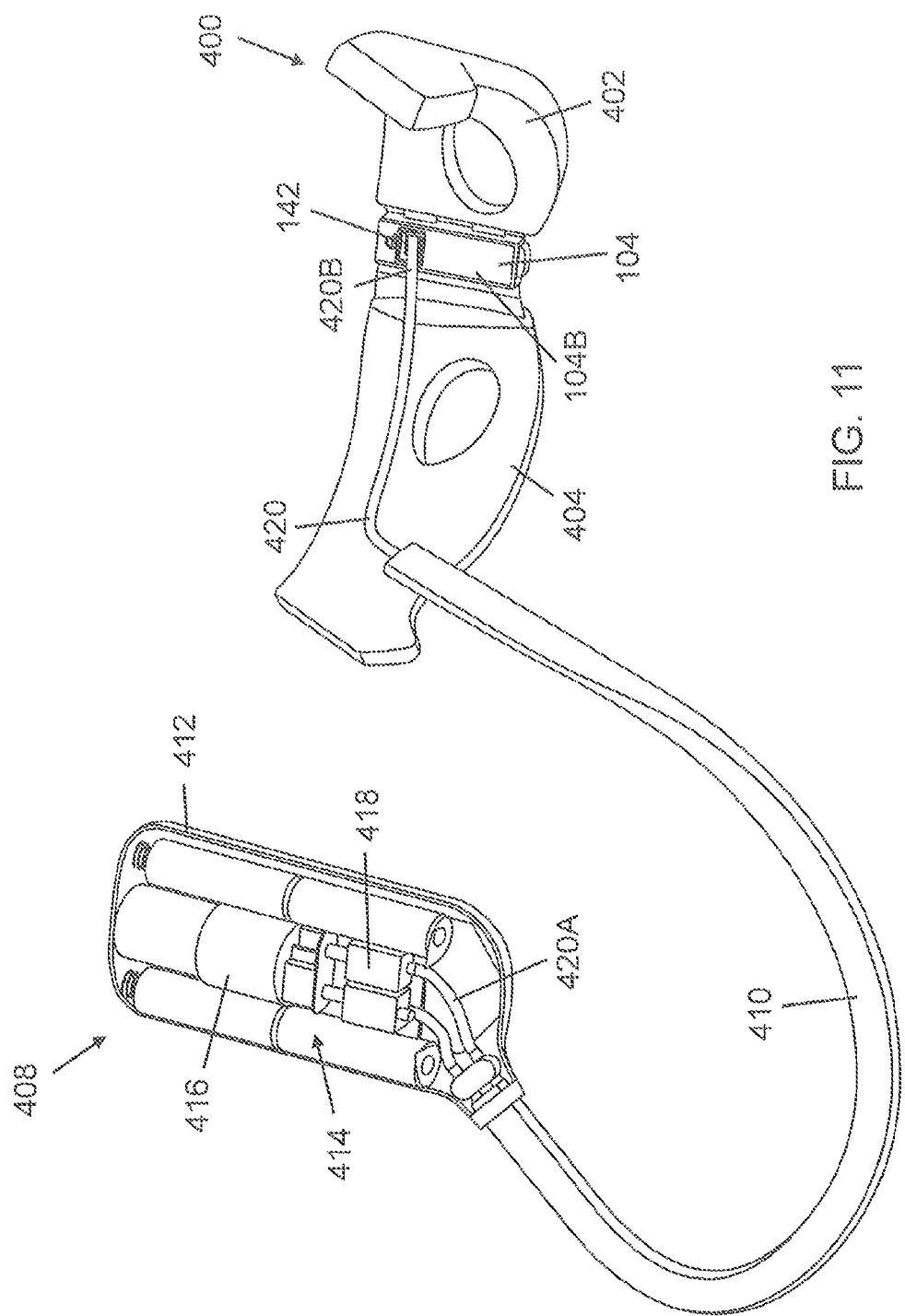
FIG. 11 is a schematic view illustrating the connection between the scent-emitting module of the eye massage apparatus with a flowing device.

Referring to FIG. 11, the eye massage apparatus 400 can be connected with an operator controller 408 via a cable assembly 410. The operator controller 408 is outside the eye massage apparatus 400, and can be used to actuate various functions of the eye massage apparatus 400, such as activating one or more massage programs on a user. The operator controller 408 can have a casing 412 in which is arranged a flowing device 414. In this embodiment, the flowing device 414 can exemplary include an air pump 416 connected with an air valve 418. The cable assembly 410 can enclose a duct 420 having two opposite ends 420A and 420B respectively connected with the air valve 418 of the air pump 416 and the opening 142 on the rear surface 104B of the housing 104. The air pump 416 can be operated to generate an air flow, which is conveyed through the duct 420 into the housing 104 for facilitating diffusion of the scent.

FIG. 12 is a schematic View illustrating a massage chair 500 including the scent-emitting module 100 or 100'. The massage chair 500 can include a seat 502, a backrest 504 assembled with the seat 502 at a rear thereof, and left and right armrests 506 disposed at the left and right sides of the seat 502. The seat 502 can provide support for a user in a sitting position. The backrest 504 can be pivotally connected with the seat 502, and can be adjustable in inclination. The backrest 504 can be assembled with a back massaging mechanism operable to apply diverse types of massage actions along the back of a user. Moreover, the backrest 504 can include a head resting region 510, and a left and a right wing portion 512 respectively protruding forward near the head resting region 510. The scent-emitting module 100 or 100' can be arranged near the head resting region 510, e.g., adjacent to one of the left and right wing portions 512. Moreover, a flowing d (not shown) as described previously may be coupled with the scent-emitting module 100 or 100' to facilitate outward diffusion of the aromatic scent. The flowing device may be arranged in the massage chair, or in an operator controller as described previously with reference to FIG. 11. Scent-emitting module 100 or 100' may be configured to emit scent in close proximity of the user. In this way, the scent would not be detected by someone beyond a certain proximity, e.g. 0.5, 1 meter from scent-emitting module 100 or 100'. Scent-emtting module 100 or 100' may be configured to release a pre-determined amount of scent, e.g. by programming the time required to open and close holes 105, so as to control the amount of emission of the scent. In this way, scent-emitting module 100 or 100 may be control to emit scent with a pre-determined range from it.

Advantages of the massage apparatuses described herein include the ability to apply massage actions and emit an aromatic scent so as to effectively relieve stress and pain and provide enhanced healing effects. As a result, a user can enjoy enhanced massage experience and obtain effective relaxation.

Realizations of the systems and methods have been described only in the context of particular embodiments. These embodiments are meant to be illustrative and not limiting. Many variations, modifications, additions, and improvements are possible. Accordingly, plural instances may be provided for components described herein as a single instance. Structures and functionality presented as discrete components in the exemplary configurations may be implemented as a combined structure or component. These and other variations, modifications, additions, and improvements may fall within the scope of the inventions as defined in the claims that follow.

What is claimed is:

1. A massage apparatus comprising:
    a massage system having a main body and a massage member, the massage member for use in performing a massage action;
    a scent-emitting module secured to the main body of the massage system, the scent-emitting module having:
        a first aromatic scent subsystem, the first aromatic scent subsystem having a first main body, the first main body having a first interior cavity, a plurality of first holes, and a first scent release actuator, the first interior cavity for housing a first scent medium, the plurality of first holes for emitting scent produced by the first scent medium, the first scent release actuator configurable to transition between a first emitting state and a first non-emitting state, the first emitting state being a state in which the plurality of first holes are not blocked by the first scent release actuator, the first non-emitting state being a state in which the plurality of first holes are blocked by the first scent release actuator;
        a second aromatic scent subsystem, the second aromatic scent subsystem having a second main body, the second main body having a second interior cavity, a plurality of second holes, and a second scent release actuator, the second interior cavity for housing a second scent medium, the plurality of second holes for emitting scent produced by the second scent medium, the second scent release actuator configurable to transition between a second emitting state and a second non-emitting state, the second emitting state being a state in which the plurality of second holes are not blocked by the second scent release actuator, the second non-emitting state being a state in which the plurality of second holes are blocked by the second scent release actuator;
        wherein each of the first and second aromatic scent subsystems are independently configurable to be in a scent-emitting state or a scent non-emitting state;
        wherein the first aromatic scent subsystem is independently configurable to be in the scent-emitting state when the first interior cavity houses the first scent medium and the first scent release actuator is transitioned to the first emitting state; and
        wherein the second aromatic scent subsystem is independently configurable to be in the scent-emitting state when the second interior cavity houses the second scent medium and the second scent release actuator is transitioned to the second emitting state; and
    a microcontroller including a memory and respectively connected with the massage system and the scent emitting module, the memory storing a massage program that contains an instruction which, when executed by the microcontroller, is operable to:
        selectively configure both the first aromatic scent subsystem and second aromatic scent subsystem to simultaneously be in a scent-emitting state by transitioning the first and second scent release actuators to be in the first and second emitting states, respectively; and
        selectively configure the first aromatic scent subsystem to be in the scent non-emitting state while the second aromatic scent subsystem is configured to be in the scent emitting state by transitioning the first scent release actuator to be in the first non-emitting state and transitioning the second scent release actuator to be in the second emitting state;
    wherein the microcontroller is further configurable to cause the massage member of the massage system to apply a massage action when the first aromatic scent subsystem and second aromatic scent subsystem are simultaneously in the scent-emitting state.

2. The massage apparatus according to claim 1, wherein when the massage system applies the massage action, and when the first and second aromatic scent subsystems receives the first scent medium and second scent medium respectively, the microcontroller is configurable to cause, based on the massage program, both the first and second aromatic subsystems to simultaneously emit the first scent medium and second scent medium.

3. The massage apparatus according to claim 1, wherein the scent-emitting module includes a housing having one or more outlet holes for scent emission outside the scent-emitting module, wherein the housing for the scent-emitting module houses the first aromatic scent subsystem and the second aromatic scent subsystem.

4. The massage apparatus according to claim 3, wherein at least one of the first and second scent release actuators includes an operating portion exposed outward for manual operation.

5. The massage apparatus according to claim 3, wherein each of the first aromatic scent subsystem and second aromatic scent subsystem further includes a scent cartridge containing the first scent medium and the second scent medium, respectively, each scent cartridge being removably installed in the housing.

6. The massage apparatus according to claim 5, wherein each of the first and second scent release actuators is spring biased to seal the first and second holes of the respective scent cartridge.

7. The massage apparatus according to claim 5, wherein the housing further includes a plurality of electric conductors, wherein each scent cartridge includes a heater, wherein each heater is electrically connected with one or more of the plurality of electric conductors when the scent cartridge that includes the heater is placed in the housing.

8. The massage apparatus according to claim 5, wherein the housing is assembled with a lid operable to open and close the housing to respectively allow and prevent access to a cavity where each scent cartridge is arranged.

9. The massage apparatus according to claim 1, wherein the scent-emitting module is connected with a flowing device via a duct, the flowing device being operable to flow air through an interior of the scent-emitting module for facilitating outward diffusion of:
- a first aromatic scent emitted by the first scent medium when the first scent release actuator is configured to be in the first emitting state; and
- a second aromatic scent emitted by the second scent medium when the second scent release actuator is configured to be in the second emitting state.

10. The massage apparatus according to claim 9, wherein the flowing device is arranged in an operator controller of the massage apparatus.

11. The massage apparatus according to claim 1, being implemented as an eye massage apparatus.

12. The massage apparatus according to claim 11, wherein the eye massage apparatus includes a left-eye portion and a right-eye portion, and a bridge connecting the left-eye portion with the right-eye portion, the scent-emitting module being arranged in a region of the bridge.

13. The massage apparatus according to any of claims 1 to 10, being implemented as a massage chair.

14. The massage apparatus according to claim 13, wherein the massage chair includes a head resting region, and a left and a right wing portion respectively protruding forward near the head resting region, the scent-emitting module being arranged in one of the left and right wing portions.

15. A method of configuring a massage apparatus, the massage apparatus having a massage system, a scent-emitting module, and a microcontroller, the massage system having a main body and a massage member, the massage member for performing a massage action, the scent-emitting module secured to the main body of the massage system, the scent-emitting module having a first aromatic scent subsystem and a second aromatic scent subsystem, the first aromatic scent subsystem having a first main body, the first main body having a first interior cavity, a plurality of first holes, and a first scent release actuator, the first interior cavity for housing a first scent medium, the plurality of first holes for emitting scent produced by the first scent medium, the second aromatic scent subsystem having a second main body, the second main body having a second interior cavity-, a plurality of second holes, and a second scent release actuator, the second interior cavity for housing a second scent medium, the plurality of second holes for emitting scent produced by the second scent medium, the method comprising:
- housing, in the first interior cavity, the first scent medium;
- housing, in the second interior cavity, the second scent medium;
- configuring the first scent release actuator to transition between a first emitting state and a first non-emitting state, the first emitting state being a state in which the plurality of first holes are not blocked by the first scent release actuator, the first non-emitting state being a state in which the plurality of first holes are blocked by the first scent release actuator;
- configuring the second scent release actuator to transition between a second emitting state and a second non-emitting state, the second emitting state being a state in which the plurality of second holes are not blocked by the second scent release actuator, the second non-emitting state being a state in which the plurality of second holes are blocked by the second scent release actuator;
- configuring each of the first and second aromatic scent subsystems to be independently configurable to be in a scent-emitting state or a scent non-emitting state;
- selectively configuring, by the microcontroller, both the first aromatic scent subsystem and second aromatic scent subsystem to simultaneously be in a scent-emitting state by transitioning the first and second scent release actuators to be in the first and second emitting states, respectively; and
- selectively configuring, by the microcontroller, the first aromatic scent subsystem to be in the scent non-emitting state while the second aromatic scent subsystem is configured to be in the scent emitting state by transitioning the first scent release actuator to be in the first non-emitting state and transitioning the second scent release actuator to be in the second emitting state.

* * * * *